US011154603B1

United States Patent
Deisseroth

(10) Patent No.: US 11,154,603 B1
(45) Date of Patent: Oct. 26, 2021

(54) BURKHOLDERIA PSEUDOMALLEI COMPOSITION

(71) Applicant: MicroVAX, LLC, Warrenton, VA (US)

(72) Inventor: Albert B. Deisseroth, Potomac, MD (US)

(73) Assignee: MicroVAX, LLC, Warrenton, VA (US)

( * ) Notice: Subject to any disclaimer, the term of this patent is extended or adjusted under 35 U.S.C. 154(b) by 0 days.

(21) Appl. No.: 15/864,268

(22) Filed: Jan. 8, 2018

Related U.S. Application Data

(63) Continuation-in-part of application No. 15/345,945, filed on Nov. 8, 2016, now abandoned.

(60) Provisional application No. 62/253,260, filed on Nov. 10, 2015.

(51) Int. Cl.

| | |
|---|---|
| A61K 39/02 | (2006.01) |
| C07K 14/195 | (2006.01) |
| C07K 14/705 | (2006.01) |
| C07K 14/47 | (2006.01) |
| A61K 39/00 | (2006.01) |

(52) U.S. Cl.
CPC ............ *A61K 39/02* (2013.01); *C07K 14/195* (2013.01); *C07K 14/4702* (2013.01); *C07K 14/70575* (2013.01); *A61K 2039/53* (2013.01); *A61K 2039/6031* (2013.01); *C07K 2319/00* (2013.01)

(58) Field of Classification Search
None
See application file for complete search history.

(56) References Cited

U.S. PATENT DOCUMENTS

| | | |
|---|---|---|
| 5,962,406 A | 10/1999 | Armitage et al. |
| 8,119,117 B2 | 2/2012 | Deisseroth et al. |
| 9,533,036 B2 | 1/2017 | Tang et al. |

OTHER PUBLICATIONS

Skolnick et al. (Trends in Biotechnology 18: 34-39, 2000) (Year: 2000).*
Andrea J. Dowling et al.: Genome-Wide Analysis Reveals Loci Encoding Anti-Macrophage Factors in the Human Pathogen Burkholderia pseudomallei K96243, PLOS ONE. Dec. 2010, vol. 5, Issue 12, 10 pages.
Mary N. Burtnick et al.: The Cluster 1 Type VI Secretion System Is a Major Virulence Determinant in Burkholderia pseudornallei, Infection and Immunity, Apr. 2011, vol. 79, No. 4, pp. 1512-1525.
A. Deisseroth et al.: TAA/ecdCD40L adenoviral prime-protein boost vaccine for cancer and infectious diseases, Cancer Gene Therapy (2013) 20, pp. 65-69.
Andrea J. Dowling: Novel gain of function approaches for vaccine candidate identification in Burkholderia pseudornallei, Frontiers in Cellular and Infection Microbiology, Jan. 9, 2013, 6 pages.
Isabelle J. Toesca et al.: The Type VI Secretion System Spike Protein VgrG5 Mediates Membrane Fusion during Intercellular Spread by Pseudomallei Group *Burkholderia* Species, Infection and Immunity, Apr. 2014, vol. 82, No. 4, pp. 1436-1444.
Leang-Chung Choh et al.: Burkholderia vaccines: are we moving forward? Frontiers in Cellular and Infection Microbiology, Feb. 5, 2013, vol. 3, Article 5, 18 pages.
Yan Ting Lim et al.: Extended Loop Region of Hcp1 is Critical for the Assembly and Function of Type VI Secretion System in Burkholderia pseudomallei, Scientific Reports 5: 8235, published Feb. 4, 2015, 10 pages.
Mark P. Stevens et al.: Attenuated virulence and protective efficacy of a Burkholderia pseudomallei bsa type III secretion mutant in murine models of melioidosis, Microbiology (2004), 150, pp. 2669-2676.
Wildaliz Nieves et al.: A naturally-derived outer-membrane vesicle vaccine protects against lethal pulmonary Burkholderia pseudomallei infection, Vaccine. Oct. 26, 2011; 29(46), 21 pages.
Sharon J. Peacock et al.: Melioidosis Vaccines: A Systematic Review and Appraisal of the Potential to Exploit Biodefense Vaccines for Public Health Purposes, PLOS Neglected Tropical Diseases, Jan. 2012, vol. 6, Issue 1, 8 pages.
Yucheng Tang et al.: Multistep process through which adenoviral vector vaccine overcomes anergy to tumor-associated antigens, Blood, Nov. 1, 2004, vol. 104, No. 9, pp. 2704-2713.
Yu Cheng Tang et al.: Use of CD40L immunoconjugates to overcome the defective immune response to vaccines for infections and cancer in the aged, Cancer Immunology, Immunotherapy (2009) 58, pp. 1949-1957.
Yucheng Tang et al.: Vector Prime/Protein Boost Vaccine That Overcomes Defects Acquired during Aging and Cancer, The Journal of Immunology, Oct. 15, 2006, 177 (8), pp. 5697-5707.

* cited by examiner

*Primary Examiner* — Robert A Zeman
(74) *Attorney, Agent, or Firm* — Jacob Frank; Glenn Snyder

(57) ABSTRACT

A cDNA composition for reducing the virulence of Bp and reduce the cell kill and scope of the infectious disease *Burkholderia pseudomallei*. (Bp), which encodes fusion proteins comprised of fragments of the extracellular domains of two Bp proteins are attached to the extracellular domain (ecd) of the potent immunostimulatory protein CD40 ligand (CD40L) in order to increase the levels of neutralizing antibodies which will interfere with the function of the extracellular domains of three Bp protein peptide fragments, OMP85, VgrG5 and Hcp-1, in order to protect against a lethal challenge of Bp.

3 Claims, 1 Drawing Sheet
Specification includes a Sequence Listing.

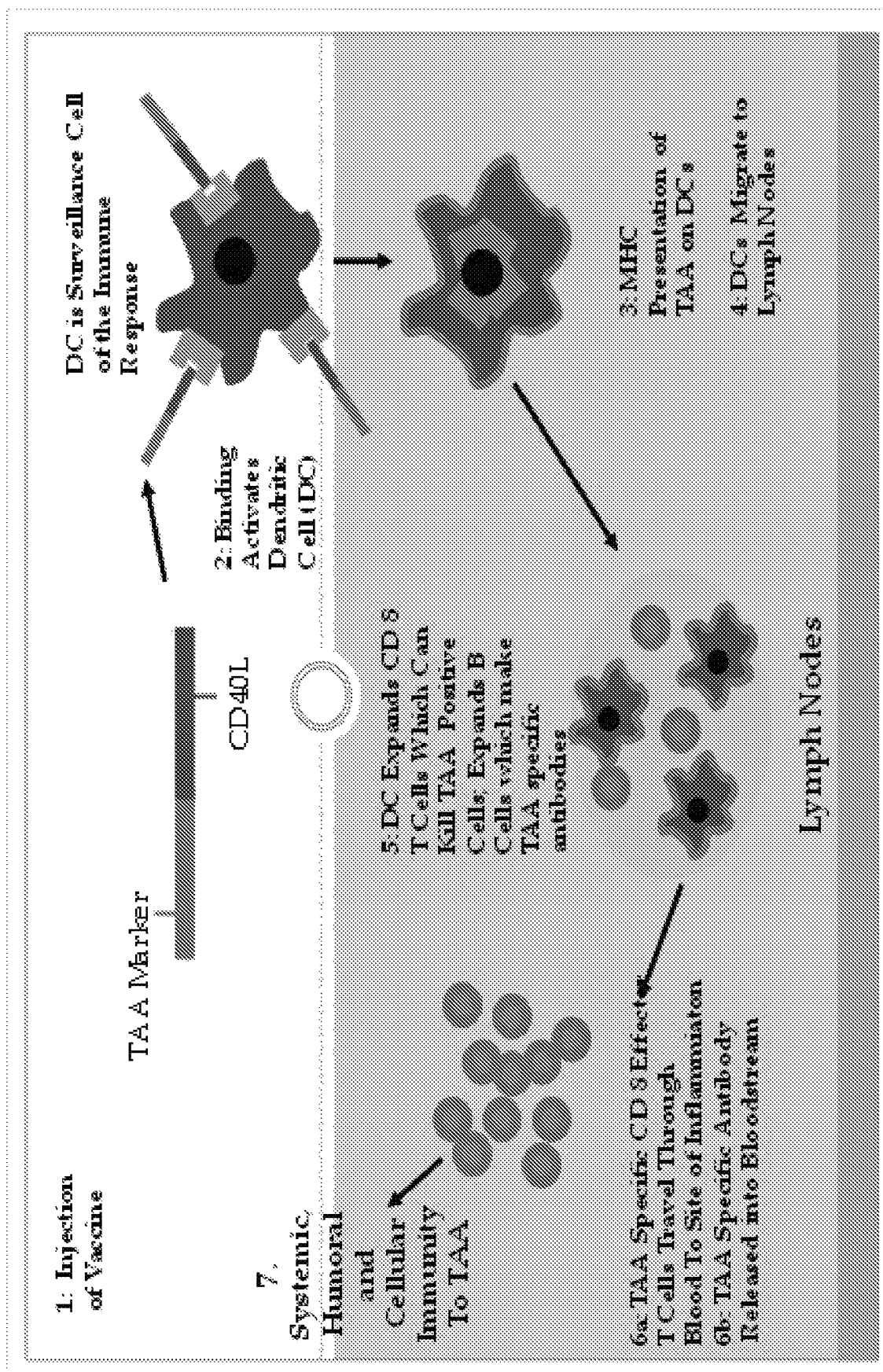

SEQUENCE LISTING

```
<160> NUMBER OF SEQ ID NOS: 4

<210> SEQ ID NO 1
<211> LENGTH: 45
<212> TYPE: PRT
<213> ORGANISM: Artificial Sequence
<220> FEATURE:
<223> OTHER INFORMATION: Synthetic Construct

<400> SEQUENCE: 1

Met Val Val Gly Asn Ile Glu Leu Thr Phe Pro Leu Pro Gly Thr Gly
1               5                   10                  15

Tyr Asp Arg Thr Leu Arg Val Phe Thr Phe Leu Asp Gly Gly Asn Val
            20                  25                  30

Trp Gly Asn Ala Pro Gly Gly Thr Ser Thr Gly Ala Asn
        35                  40                  45

<210> SEQ ID NO 2
<211> LENGTH: 53
<212> TYPE: PRT
<213> ORGANISM: Artificial Sequence
<220> FEATURE:
```

```
<223> OTHER INFORMATION: Synthetic Construct

<400> SEQUENCE: 2

Phe Met Ile Val Ser Gly Leu Ala Asn Ala Gly Ser Ala Ala Ala Ala
1               5                   10                  15

Ala Gly Leu Ile Lys Gly Gly Gly Lys Leu Ala Asp Leu Pro Trp Ala
                20                  25                  30

Gly Phe Gly Ile Ser Ala Ala Gln Phe Ala Gly Ala Thr Gly Val Ser
            35                  40                  45

Thr Ala Leu Met Ala
    50

<210> SEQ ID NO 3
<211> LENGTH: 27
<212> TYPE: PRT
<213> ORGANISM: Artificial Sequence
<220> FEATURE:
<223> OTHER INFORMATION: Synthetic Construct

<400> SEQUENCE: 3

Phe Lys Asn Asp Tyr Asp His Pro Ala Arg Leu Gln Glu Gly Leu Thr
1               5                   10                  15

Pro Ala Ala Ala Arg Gly Thr Ile Thr Leu
                20                  25

<210> SEQ ID NO 4
<211> LENGTH: 17
<212> TYPE: PRT
<213> ORGANISM: Artificial Sequence
<220> FEATURE:
<223> OTHER INFORMATION: Synthetic Construct

<400> SEQUENCE: 4

Asp His Pro Ala Arg Leu Gln Glu Gly Leu Thr Pro Ala Ala Ala Ala
1               5                   10                  15

Arg
```

BURKHOLDERIA PSEUDOMALLEI COMPOSITION

CROSS-REFERENCE TO RELATED APPLICATIONS

This application is a continuation-in-part of U.S. patent application Ser. No. 15/345,945 filed Nov. 8, 2016, now abandoned, which claims priority and the benefit under 35 USC paragraph 119(e) of U.S. Provisional Patent Application No. 62/253,260 filed on Nov. 10, 2015, the disclosure of which are both hereby incorporated by reference herein.

FIELD OF THE INVENTION

The present invention relates generally to the field of compositions and more specifically to a composition for the infectious disease *Burkholderia pseudomallei*.

BACKGROUND OF THE INVENTION

*Burkholderia pseudomallei* (Bp): The reservoir for Bp is contaminated soil and water and animals: cats. sheep, goats, and horses in Thailand, Laos, Singapore, Malaysia, Burma, Vietnam, China, Taiwan, northern Australia, and to a lesser extent India, Central and South America, Africa, and the Middle East (1-2). In Thailand, 80% of children are positive for antibodies to Bp antigens. The severity of the infection depends on host factors such as diabetes, renal failure, chronic lung disease and alcohol use (1). At a variable time after exposure, the infection presents with fever, pain the location of which depends on the location of the organ affected (e.g. pleuritic chest pain with the common pulmonary form, bone or joint pain with osteomyelitis or septic arthritis), formation of abscesses, bacteremia (60%), septic shock (20%), and 90% mortality if not treated with antibiotics. Bp is resistant to most antibiotics (3), and evolves resistance rapidly. It is the third most common cause of death due to infectious diseases in Thailand (behind HIV and TB) and is projected to overtake TB in the near future (4). Pb is a facultative intracellularly replicating gram negative rod which is requires long term antibiotic treatment to completely eradicate the infection, with recurrences up to 40 years later (5). Its ability to replicate and survive inside macrophages for such longtime periods suggest that Bp has evolved virulence factors that can overcome the intracellular defense mechanisms of the macrophage against infection.

The steps involved in the life cycle of Bp are as follows (6-9):

1. Entry into the human subject following exposure through breaks in the skin, inhalation of aerosols or ingestion.

2. For the cutaneous route, Bp then attaches to either epithelial cells or macrophages and enters the epithelial cell through endocytosis or is phagocytosed by macrophages (6).

3. Escape from the endosome into the cytoplasm (6-9) which is dependent on the Type 3 secretion systems (T3SS) occurs next.

4. The formation of Multi-Nucleated Giant Cells (MNGC) induced by the interaction of the Bp with the plasma membrane of other neighboring cells through the plasma membrane of the infected cell is dependent on the PipB protein of the T3SS system and the VgrG5 protein of the TSS-6 system (7-11). Toesca (12) has shown that the $AA_{651-696}$ carboxyterminal amino acids in the extracellular domain of the VgrG5 transmembrane protein (which is on the outside of the infected cell) are necessary for the induction of the fusion of the plasma membrane of the infected cell with that of the neighboring cells to form the MNGC. The formation of the MNGC is thought to be part of the mechanism through which Bp can replicate, spread from cell to cell, and to evade the host immune response (12). Truncation mutants of the VgrG5 protein, especially those which involve truncation mutations (deletions) which involve loss of AA 651-696 result in loss of the cell fusion activity of VgrG5 as well as reduce the cytotoxicity of Burk for target cells (12).

5. The hemolysin-coregulated proteins (Hcp-1 and Hcp-2) are both substrates for as well as structural components of the Type GVI Secretion System cluster 1 (T6SS1) which is essential for the virulence of *B pseudomallei* (13). The T6SS apparatus is a secretory tube or channel through which the Burk secretes toxins (virulence factors) into the cytoplasm of cells which it has infected (13). Hcp proteins are required for assembly of the T6SS as well as the chaperoning of toxins and itself through the T6SS into the cytoplasm of the infected cell (14). The Hcp-1 proteins form hexameric rings which stack in parallel array into tubes for secretion (14). Hcp-1 has an extended loop (AA40-AA56) which may act as a key contact point between adjacent hexameric rings (14). Replacement of two amino acid residues in this loop totally prevents formation of the T6SS and in turn inhibits formation of multinucleate giant cells during infection (14). It is possible that the induction of neutralizing antibodies to this loop fragment of Hcp-1 would disrupt the formation of the hexameric secretory apparatus as well, which would decrease the virulence of the Bp.

Hcp bind to the surface of antigen presenting cells, perhaps explaining their striking immunogenicity (13). Hcp-1 has been shown on an immunoblot to be recognized by sera from melioiidosis patients which are present at high titers in these patients. Whitlock et al reported that 75% of mice vaccinated with recombinant Hcp1 from *B. mallei* are protected in a challenge experiment (13). Choh et al (15) reports that vaccination with Hcp-2 results in 80% survival rate to a lethal challenge with *B pseudomallei* whereas vaccination with mice vaccinated with Hcp1 results in 50% survival at 42 days (15).

The potential for high mortality without effective antibiotic therapy, the high level of resistance to most antibiotics, the rapid evolution of resistance, the ease of delivery of Bp, the fact that there is no effective composition and/or vaccine, and the fact that Bp is readily available, has contributed to its being considered a bioterrorist threat (4).

BRIEF DESCRIPTION OF THE DRAWING

FIG. 1 illustrates an overview of TAA/ecdCD40L vaccine platform for application in infectious diseases, in which a fragment of the target associated antigen (TAA) is attached to extracellular domain (ecd) of the potent immunostimulatory antigen CD40L.

DETAILED DESCRIPTION OF THE INVENTION

In this specification, although the preferred embodiments have been described in detail, it should be understood that various changes, substitutions and alterations may be made therein without departing from the spirit and scope of the invention. Therefore, the specification is to be regarded in an illustrative rather than a restrictive sense.

The use of the terms "a" and "an" and "the" and similar referents in the context of describing the invention are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in a suitable order unless otherwise indicated herein or otherwise clearly contradicted by context.

As used herein, the term "antigen" refers broadly to any antigen or portion thereof to which a human, mammal, bird or other animal can generate an immune response. "Antigen" as used herein refers broadly to a molecule that contains at least one antigenic determinant to which the immune response may be directed. The immune response may be cell-mediated, humoral or both.

As used herein, "antigenic determinant" refers to a single antigenic site or epitope on a complex antigenic molecule or particle, a minimal portion of a molecule that interacts with an antibody or T cell receptor. Antigenic determinants may be linear or discontinuous. "Pharmaceutically acceptable" in the context of the present invention means a pharmaceutical composition that is generally safe, non-toxic and biologically acceptable for veterinary and human pharmaceutical use. Preferred compositions of this invention are intended for humans or animals.

The phrase "an effective amount" is with reference to administering the fusion protein or an expression vector encoding that protein, is an amount that results in an increase in the immune response as measured by an increase in T cell activity or antibody production.

The fusion protein recited herein may be formulated with an adjuvant to enhance the resulting immune response. As used herein, the term "adjuvant" in the context of the instant invention means a chemical that, when administered with the expression vector or the fusion protein, enhances the immune response. An adjuvant is distinguished from a carrier protein in that the adjuvant is not chemically coupled to the antigen. Adjuvants are well known in the art and include, but not limited to, mineral oil emulsions (U.S. Pat. No. 4,608,251) such as Freund's complete or Freund's incomplete adjuvant (Freund, *Adv. Tuberc. Res.* 7:130 (1956); Calbiochem, San Diego Calif.), aluminum salts, especially aluminum hydroxide or ALHYDROGEL (approved for use in humans by the U.S. Food and Drug Administration), muramyl dipeptide (MDP) and its analogs such as [Thr$^1$]-MDP (Byersand Allison, Vaccine 5:223 (1987)), monophosphoryl lipid A (Johnson et al., *Rev. Infect. Dis.* 9:S512 (198)), and the like.

The term "vector" which contains a transcription unit (aka the "expression vector") as used herein refers to viral and non-viral expression vectors that when administered in vivo can enter target cells and express an encoded protein. Viral vectors suitable for delivery in vivo and expression of an exogenous protein are well known and include adenoviral vectors, adeno-associated viral vectors, retroviral vectors, vaccinia vectors, pox vectors, herpes simplex viral vectors, and the like. Viral vectors are preferably made replication defective in normal cells. For example, see U.S. Pat. Nos. 6,669,942; 6,566,128; 6,794,188; 6,110, 744; 6,133,029. The vector can be administered parenterally, such as intravascularly, intravenously, intra-arterially, intramuscularly, subcutaneously, or the like. Administration can also be orally, nasally, rectally, transdermally or aerosol inhalation. The vectors may be administered as a bolus, or slowly infused. The vector is preferably administered subcutaneously. Plasmid expression vectors which contain transcription units which encode the TAA/ecdCD40L fusion protein may also be injected subcutaneously or intramuscularly to vaccinate subjects.

The term "transcription unit" as it is used herein in connection with an expression vector means a stretch of DNA that is transcribed as a single, continuous mRNA strand by RNA polymerase, and includes the signals for initiation and termination of transcription. For example, in one embodiment, a transcription unit of the invention includes nucleic acid that encodes from 5' to 3' a secretory signal sequence, a Bp antigen and CD40 ligand. The transcription unit is in operable linkage with transcriptional and/or translational expression control elements such as a promoter and optionally any upstream or downstream enhancer element(s). A useful promoter/enhancer is the cytomegalovirus (CMV) immediate-early promoter/enhancer. See U.S. Pat. Nos. 5,849,522 and 6,218,140.

The term "CD40 ligand" (CD40L) as used herein refers to a full length or portion of the molecule known also as CD154 or TNF5. CD40L is a type II membrane polypeptide having a cytoplasmic domain at its N-terminus, a transmembrane region and then an extracellular domain (ecd) at its C-terminus. Unless otherwise indicated the full length CD40L is designated herein as "CD40L," "wtCD40L" or "wtTmCD40L." The nucleotide and amino acid sequence of CD40L from mouse and human is well known in the art and can be found, for example, in U.S. Pat. No. 5,962,406. Also, included within the meaning of CD40 ligand are variations in the sequence including, but not limited to, conservative amino acid changes and the like which do not alter the ability of the ligand to elicit an immune response in conjunction with the fusion protein of the invention.

The term "neutralizing antibody" as used herein refers to antibodies that reduce the virulence, infectivity or pathogenicity of Bp by partial or complete destruction of one or more Bp virulence antigenic factor.

Some of the abbreviations used herein include: "Ad" (adenoviral); "sig" (signal sequence); "TAA" (target associated antigen); "ET" (epitope target); "ecd" (extracellular domain); and "sc" (subcutaneous).

Available Bp compositions and/or vaccines: Vaccine development for Bp has recently been reviewed (16). Following is a list of the vaccine strategies being pursued:

A. Whole cell vaccines: the advantage is that they potentially can immunize the host against many antigens which is important given the genetic diversity of Bp. The disadvantages include the significant side effects and the need for adjuvants (16). With adjuvants, these vaccines are protective in animal models (16).

B. Attenuated vaccines: A Bp vaccine which carries mutations in the T3SS apparatus has been reported to be protective in a highly susceptible mouse model (17). The risk of reversion to a more aggressive phenotype makes attenuated vaccines unattractive for the foreseeable future.

C. Bp derived Outer Membrane Vesicles (OMV) released from many Gram-negative bacteria: OMV derived from Bp have been shown to protect Balb/c mice from aerosol delivery of a lethal dose of Bp (18).

D. Subunit composition: The Outer Membrane Protein OMP85 (of the OMP85 protein family) which is part of the OMV, induces protective immunity in 70% of Balb/c mice vaccinated with BPSL2151 (OMP85) against a lethal challenge with Bp (19). The region in the extracellular domain of OMP85 which is the target of the antibodies induced by the vaccine is from AA 681-719 (19). This extracellular fragment sequence including additional several amino acids at the beginning and end is SEQ ID NO I-AA679-MVVGN-IELTFPLPGTGYDRTLRVFTFLDGGNVWGNAPGGT-STGAN-AA723 This sequence is from GenBank accession number EF409943.1.

A New Direction for Bp Composition/Solution. A cDNA composition which encodes fusion proteins comprised of peptide fragments of the extracellular domains of three Bp proteins (OMP85, VgrG5, and Hcp-1) are attached to the extracellular domain (ecd) of the potent immunostimulatory protein CD40 ligand (CD40L) to increase the levels of antibodies which will interfere with the function of the extracellular domains of the three Bp proteins cited above, OMP85, VgrG5, and Hcp-1 in order to protect against a lethal challenge of Bp.

Fragment of the Extracellular Domain on BPSL2151 (a Bp Protein of the OMP85 Family) Proposed for Target of Bp Composition. On the basis of the information summarized above (19), we are proposing to attach the peptide fragment from amino acid 681-719 of the BPSL2151 (OMP85) protein (SEQ ID NO I-AA679-MVVGNIELTFPLPGTGY-DRTLRVFTFLDGGNVWGNAPGGTSTGAN-AA723. $AA_{679}$-$AA_{723}$, to the ecdCD40L to generate the first composition.

C-Terminal Fragment of the Extracellular Domain of the VgrG5 Protein Proposed for Target of Bp Composition: Two studies have reported the induction of high levels of the Bp VgrG1 protein in macrophages infected with Bp (20-21). Toesca et al (6, 12) have reported that the carboxyl terminal end (AA651-AA703) of the extracellular domain of the VgrG5 protein SEQ ID NO 2-AA651-FMIVSGLANAGSAAAAAGLIKGGGKLADLPWAGF-GISAAQFAGATGVSTALMA-AA703) is necessary and may trigger the fusion of the membrane of the infected cell with neighboring cells to promote the formation of MNGCs. The amino acid sequence in the carboxyterminal end of VgrG5 is known to be conserved across all *Burkholderia* species (12). Accordingly, we are proposing to attach the peptide fragment from amino acid 651-703 of the VgrG5 protein to the ecd of CD40L to generate the second composition.

The Extended Loop (AA35-AA61) of the Hcp-1 Protein Proposed as Target for Bp Composition: As described above, vaccination of mice with Hcp-1 and Hcp-2 (13, 15) results in protection of the test mice to a lethal challenge with Bp. We are proposing to rely on the structural data presented by Lim et al (see reference 14) on the role of the extended loop (AA40-56) in Hcp1 in the assembly of the T6SS1 hexameric secretary apparatus, the evidence that loss of this loop reduces the virulence of *B pseudomallei*, and that the Hcp-1 protein is very immunogenic to choose the extended loop (AA35-AA65) as an antigenic target for the fusion protein comprised of the AA35-AA65 fragment of the Hcp-1 attached to ecdCD40L. We are proposing to create a composition by attaching a 25 AA fragment (see SEQ ID NO 3 below) which contains the 15 AA core of the extended loop (from Asp40-Arg56-see SEQ ID NO 4 below)) region of Hcp1 (loop I2,3 in FIG. 1 of reference 14) to the ecdCD40L. We will insert a transcription unit that encodes this into a plasmid expression vector. SEQ ID NO. 3 is a peptide fragment selected because, as pointed out, like peptide fragments SEQ ID NOS 1 and 2, it induces neutralizing antibodies and accordingly it is recognized by and bound to MHC Class II.

SEQ ID No 3:
AA35-FKNDYDHPARLQEGLTPAAAARGTITL-AA61
SEQ ID NO 4:
AA40-DHPARLQEGLTPAAAAR-AA56

TAA/ecdCD40L Vaccine Induces High Titers of Neutralizing Antibodies. Applicant has developed a TAA/ecdCD40L vaccine platform, illustrated in FIG. 1, for use in preventing infectious diseases, in which a fragment of the target associated antigen (TAA) is attached to extracellular domain (ecd) of the potent immunostimulatory antigen CD40L (22-26). The attachment of the TAA to the ecdCD40L is designed to promote presentation of TAA on Class I as well as Class II MHC and provide helper function thereby overcoming the defective response to vaccination in immunosuppressed, debilitated patients including those who are of advanced chronological age. The attachment of the TAA to the ecdCD40L will also increase the potency of antigens which are weak immunogens to increase the titer of antibodies which will block the function of extracellular virulence proteins of the bacterial cell target (22-26). The TAA/ecdCD40L also induces a potent cellular immune response against foreign antigens on infectious agents (25). The TAA/ecdCD40L vaccine platform has shown to induce robust immune responses against 7 different antigenic targets associated with both cancer cells as well as infectious agents. A phase I clinical trial of a TAA/ecdCD40L cancer vaccine is currently under way (26). A fusion protein vaccine comprised of 2 fragments from the region of the H5N1 influenza hemagglutinin protein which binds cellular receptors attached to the ecdCD40L induced neutralizing antibody titers for influenza virus of over $\frac{1}{4500}$ (25). The robustness of both the humoral as well as the cellular immune response induced by the TAA/ecdCD40L vaccine platform, as well as the high titers of antibodies induced against foreign antigens on infectious agents suggest that a TAA/ecdCD40L vaccine which targets epitopes in the OMP85, VgrG5, and Hcp-1c proteins would be valuable both to prevent infection as well as reduce the tissue damage and mortality of individuals already infected with Bp.

TAA/ecdCD40L Composition for Bp. We will construct three expression plasmid cDNA transcription units, each comprised of a CMV promoter linked to a secretory sequence (sig) which is linked to one of the following fragments of Bp transmembrane proteins (which were described above in Section 4) each of which is attached to a 9 AA linker which is attached to the ecdCD40L:

a. Peptide Fragment 1: OMP85 AA 679-723 SEQ ID NO I: SEQ ID NO I-AA679-MVVGNIELTFPLPGTGY-DRTLRVFTFLDGGNVWGNAPGGTSTGAN-AA723.

b. Peptide Fragment 2: The 53 AA at the carboxyterminus of the VgrG5 protein (SEQ ID NO 2-AA651-FMIVSGLANAGSAAAAAGLIKGGGKLADLPWAGF-GISAAQFAGATGVSTALMA-AA703).

c. Peptide Fragment 3: The 25 AA fragment of the extended loop of the Hcp-1 protein (SEQ ID NO 3-AA35-FKNDYDHPARLQEGLTPAAAARGTITL-AA61.

The plasmid expression vectors which encode each of the fusion proteins generated by attachment of each one of these peptide fragments to the ecdCD40L will be designated as follows:

a. Composition I: $pBpOMP85_{679-723}$/ecdCD40L
b. Composition II: $pBpVgrG5_{651-703}$/ecdCD40L
C. Composition III: $pHcp1_{35-61}$/ecdCD40L These three plasmid expression vectors will be administered intramuscularly (IM) individually or as a 1:1 mixture of these two plasmids on Days 1, 7 and 21.

Rationale for Burk Vector Composition Strategy: Bp evades the human immune response enabling it to spread from cell to cell, which increases the number of cells which contain actively replicating Bp, which ultimately increases the number of host cells killed during a Bp infection through the action of two proteins:

1. OMP85 (BPSL2151), is an 89,032 kDa protein outer membrane protein which has been shown to be essential for bacterial cell viability; it has also been shown to be essential for positioning and folding of other outer membrane proteins (19). Since this protein is highly immunogenic and is highly conserved with respect to amino acid sequence among all *Burkholderia* species, we chose a peptide fragment of this protein (see SEQ ID NO 1) attached to ecdCD40L as a target for a universal composition (19).

2. The carboxy-terminal end of the VgrG5 protein is expressed on infected cells with the carboxyl-terminal end projecting from the outer surface of Bp (12). This protein triggers the fusion of cells which are infected by Bp with uninfected cells, thereby creating Multi-Nucleated Giant Cells (MNGC). The creation of these MNGC from infected macrophages, which supports the intracellular replication of Bp, creates a sanctuary for the Bp, thereby protecting it from the immune response of the host, and promotes spreading to cell and increasing the number of host cells which are killed in an infection by Bp (12). Therefore, a peptide fragment (see SEQ ID NO 2) attached to ecdCD40L has been proposed as a composition for Bp.

3. The extended loop region of the Hcp-1 protein has been shown to be necessary for the assembly of the T6SS1 hexameric secretory apparatus has been shown to be necessary for secretion of toxins from the Bp to the cytoplasm of cell which the Bp has infected (14). Mutational change of the AA sequence in the extended loop has been shown to result in prevention of the formation of the T6SS1 secretory apparatus (14). Vaccination of mice with intact Hcp-1 protein has been shown to protect them from a lethal challenge with Bp (13). Therefore, the extended loop peptide fragment of Hcp-1 (SEQ ID NO 3) attached to ecdCD40L is being proposed as a composition for Bp.

Toesca (12) has shown that the AA651-696 carboxyterminal amino acids in the extracellular domain of the VgrG5 transmembrane protein (which is on the outside of the infected cell) are necessary for the induction of the fusion of the plasma membrane of the infected cell with that of the neighboring cells to form the MNGC. Truncation mutants of the VgrG5 protein, especially those which involve truncation mutations (deletions) which involve loss of AA 651-696 result in loss of the cell fusion activity of VgrG5 as well as reduce the cytotoxicity of Burk for target cells (12).

Therefore, we have chosen the extracellular domain of the VgrG5 ($AA_{651-696}$ carboxyterminal amino acids), which is SEQ ID NO. 2, as the target for our second composition by proposing to link it to the ecd of the CD40L. The induction of antibodies and antigen specific T cells against the $AA_{651-696}$ carboxyterminal amino acids of the VgrG5 protein will block the "fusogenic" function of the VgrG5 protein, thereby preventing the formation of the MNGCs and reducing the cytotoxic effect of the Bp for infected cells.

Finally, we have chosen a fragment (AA35-AA61) of the extended loop of Hcp-1 (see SEQ ID NO 3) as the target for our third composition by proposing to link it to the ecd of the CD40L.

The composition strategy proposed above (attaching fragments of OMP85, VgrG5 and Hcp-1) has been chosen to reduce the virulence of Bp, and to block the mechanisms through which Bp protects itself from the host immune response and kills the cells which it infects.

By inducing neutralizing antibodies against these three Bp proteins, the composition will dramatically reduce the virulence of Bp and reduce the cell kill and scope of the infection (12). The choice of the ecd of the OMP85, the ecd of the VgrG5 and the extended loop of the Hcp-1 protein is a unique strategy. The combination of OMP85, VgrG5 and Hcp-1 has never been chosen together before. In addition, each of these ecd domains will be separately attached to the ecdCD40L, and then administered together, in order to magnify the degree to which a composition based on these two proteins will induce both an antigen specific humoral as well as a cellular immune response against the Bp organism and provide protection for individuals against infection by Bp.

Summary of Advantages of TAA/ecdCD40L Composition: Based on the pre-clinical studies of the TAA/ecdCD40L in TAA transgenic mouse models, the following advantages can be identified for the TAA/ecdCD40L composition strategy as compared to existing vaccine/composition strategies:

1. The TAA/ecdCD40L composition only requires 3 weeks to administer to induce a potent response due to the linkage to the ecdCD40L, thereby making it useful for use in containment of outbreaks in a local geographical area;
2. TAA/ecdCD40L overcomes anergy that may arise in the highest risk patients with chronic diseases;
3. TAA/ecdCD40L induces higher titers of antibodies which are either protective;
4. The safety concerns with the attenuated Bp vaccine strains will not exist with the TAA/ecdCD40L composition proposed above;
5. The composition would work better in older subjects (greater than 55 years) in which age group vaccines do not induce a fully protective immune response (22);
6. Two vector injections produce a memory response for at least a year (22);
7. Vector composition stable when frozen for up to 7 years.

REFERENCES

1. Gilad J, Schwartz D, and Amsalem Y. Clinical fdatres and laboratory diagnosis of infection with *Burkholderia pseudomallei*. Int J of Biomedical Science 3: 144-151, 2007.
2. Vuddhakul V, Tharavichitkul P, Na-Ngam N et al. Epidemiology of *B pseudomallei* in Thailand. Am J Trop Med Hyg 60: 458-461, 1999.
3. Schweizer H P. Mechanisms of antibiotic resistance in *Burkholderia pseudomallei*. Future Microbiol. 7: 13898-1399, 2012. Am J Trop Med Hyg 82: 113-117, 2010
4. Limmathurotsakul D, Wongratanacheewin S, Teerawatanasook N et al. Increasing incidence of human melioidosis in Northeast Thailand.
5. Gan Y H. Interaction between *B pseudomallei* and the host immune response. JID 192: 1845-1850, 2005.
6. French C, Toesca I J, Wu T H et al. Dissection of the *Burkholderia* intracellular life cycle. PNAS 108: 12095-12100, 2011.
7. Suparak S, Kespichayawattana W, Haque A, et al. MNGC formation in host cells is mediated by *Burkholderia pseudomallei* Type III secretion protein BipB. J. Bacteriol. 188: 6556-6560, 2005.

8. Kespichayawattana W, Rattanachetkul S, Wanun T et al. *Burkholderia pseudomallei* induces cell fusion and actin-associated membrane protrusion: a mechanism for cell to cell spreading. Infection and Immunity 68: 5377-5384, 2000.
9. Gan Y H, Chua K L, CHua H H, et al. Characterization of *Burkholderia pseudomallei* infection and identification of novel virulence factors. Molecular Microbiology 44: 1185-1197, 2002.
10. Burtnick M N, Brett P J, Harding S V et al. The cluster 1 type VI secretion system is a major virulence determinant in *Burkholderia pseudomallei* Infection and Immunity 79: 1512-1525, 2011.
11. Schnell M A, Ulrich R L, Ribot W J e al. Type VI secretion is a major virulence determinant in *Burkholderia mellei*. Molecular Microbiology 64: 1466-1485, 2007.
12. Toesca I. J. The Type VI Secretion System Spike Protein VgrG5 Mediates Membrane Fusion During Intercellular Spread by *pseudomallei* Group *Burkholderia* Species, Infection & Immunity, April 2014, Volume 82, Number 4.
13. Burtnick M N, Brett P J, Harding S V et al. The cluster 1 type VI secretion system is a major virulence determinant in Bp. Infection and Immunity 79: 1512-1525, 2011.
14. Lim Y T, Jobichen C, Wong J et al. Extended loop region of Hcp-1 is critical for the assembly and function of type VI secretion system in Bp. Scientific Reports 5: 8235, DOI: 10.1038/srep08235, Feb. 4, 2015, pp 1-10.
15. Choh L C, Ong G H, Vellasamy K M et al. *Burkholderia* vaccines: are we moving forward? Frontiers in Cellular and Infection Microbiology 3: 1-18 (article 5), 2013, DOI: 10.3389/fcimb.2013.00005.
16. Peacock S J, Limmathurotsakul D, Lubell Y et al. Melioidosis vaccines. PLoS Neglected Tropical Diseases. 6: e1488, 2012.
17. Stevens M P, Haque A, Atkins T et al. Attenuated virulence and protective efficacy of a *Burkholderia psedomallei* bsa type III secretion mutant in murine models of melioidosis. Microbiology 150: 2660-2676, 2004.
18. Nieves W, Asakra S, Qazi O et al. A naturally derived outer membrane vesicle vaccine protects against lethal pulmonary *Burkholderia pseudomallei* infection. Vaccine 29: 8381-8389, 2011.
19. Su Y C, Wan K L, Mohamed R, and Nathan S. Immunization with the *Burkholderia pseudomallei* outer membrane protein OMP85 induces protective immunity in mice. Vaccine 28: 5005-5011, 2010.
20. Dowling A J, Wilkinson P A, Holden M T G, et al. Genome-wide analysis reveals loci encoding anti macrophage factors in *Burkholderia pseudomallei*. PLoS One 5: 315693, 2020.
21. Dowling A J. Novel gain of function approaches for vaccine candidate identification in *Burkholderia pseudomallei*. Frontiers in Cellular and Infection Microbiology. 2: 1-5, 2013.
22. Zhang L, Tang Y, and Deisseroth A: Adenoviral vectors encoding a secretable HPV 16 E7/CD40 ligand fusion protein induce immunity for up to one year in a murine model. PNAS, 100: 15101-15106, 2003.
23. Tang, Y, Zhang, L, Yuan, J, Maynard, J, and Deisseroth, A. Multi-step process of vector mediated activation and tumor antigen loading of APC by CD40 ligand/tumor antigen secretory protein generates protection from cancer cell lines. Blood, 104: 2704-2713, 2004.
24. Tang, Y C, Maynard J, Akbulut H, Fang X M, Zhang W W, Xia X Q, Koziol J, Linton P J, and Deisseroth A. Vector Prime/Protein Boost Vaccine Which Overcomes Defects Acquired During Aging and Cancer. J. Immunology, 177:5697-5707, 2006.
25. Tang, Y C, Linton, P J, Thoman M, and Deisseroth A. Symposium in Writing: Vaccine for Infections and Cancer. Cancer Immunology Immunotherapy 58: 1949-1957, 2009.
26. Deisseroth A, Tang Y C, Zhang L, Akbulut H, and Habib N. TAA/ecdCD40L adenoviral prime-protein boost vaccine for cancer and infectious diseases. Cancer Gene Therapy 20: 65-69, 2013.
27. French C T. Protein secretion systems of *Burkholderia* species and their roles in virulence. PhD Thesis in Microbiology, Immunology and Molecular Genetics at UCLA, Chapter 5, p. 190-196, 2012.

The invention claimed is:

1. A pharmaceutical composition comprising three separate expression vectors each encoding one of three distinct fusion proteins including a Target Associated Antigen (TAA) fused to an extracellular domain (ecd) of a human CD40 ligand (CD40L), a TAA/ecdCD40L for generating a humoral and cellular immune response against an infection caused by *Burkholderia pseudomallei* (Bp) in an individual, comprising:

the first expression vector encoding a fusion protein comprising the TAA peptide fragment consisting of the sequence of SEQ ID NO. 1 from the extracellular domain of an Outer Membrane Protein 85 (OMP85) linked to the extracellular domain of a CD40L, the second expression vector encoding a fusion protein comprising the TAA peptide fragment consisting of the sequence of SEQ ID NO. 2 from the extracellular domain of a Valine-glycine repeat G5 protein (VgrG5) linked to the extracellular domain of a CD40L, and the third expression vector encoding a fusion protein comprising the TAA peptide fragment consisting of the sequence of SEQ ID NO. 3 from the extracellular domain of a hemolysin coregulated protein (Hcp-1) linked to the extracellular domain of a CD40L.

2. A pharmaceutical composition according to claim 1 wherein said first, second and third expression vectors are viral vectors.

3. A pharmaceutical composition according to claim 1 wherein said first, second and third expression vectors are plasmid DNA vectors.

* * * * *